United States Patent [19]

Osborne

[11] Patent Number: 5,158,662
[45] Date of Patent: Oct. 27, 1992

[54] DEVICE FOR DETECTING AND CONTINUOUSLY MEASURING THE CONCENTRATION OF OXIDIZABLE BIODEGRADABLE SUBSTRATES IN A MEDIUM AND METHOD

[76] Inventor: Philip S. Osborne, 602 Jenkins, Norman, Okla. 73069

[21] Appl. No.: 615,759

[22] Filed: Nov. 19, 1990

[51] Int. Cl.$^5$ .................. G01N 27/46; C12Q 1/04
[52] U.S. Cl. .................. 204/403; 204/153.12; 204/153.16; 204/284; 204/294; 435/817; 435/29; 435/4
[58] Field of Search ............. 204/153.12, 153.2, 403, 204/284, 294, 153.16; 435/4, 29, 817

[56] References Cited

U.S. PATENT DOCUMENTS

| 3,329,599 | 7/1967 | Brewer | 204/195 |
| 3,403,081 | 9/1968 | Rohrback et al. | 204/1 |
| 3,502,559 | 3/1970 | Alexander | 204/195 |
| 3,539,455 | 11/1970 | Clark, Jr. | 204/153.12 |
| 3,659,193 | 4/1972 | Pitsch et al. | 324/29 |
| 3,868,223 | 2/1975 | Robock et al. | 23/253 R |
| 4,105,523 | 8/1978 | Stolarczyk | 204/195 B |
| 4,258,316 | 3/1981 | Leif | 324/71 CP |
| 4,288,544 | 9/1981 | Suzuki et al. | 204/153.12 |
| 4,321,322 | 3/1982 | Ahnell | 435/34 |
| 4,384,936 | 5/1983 | Obana et al. | 204/403 |
| 4,983,516 | 1/1991 | Turner et al. | 435/34 |

FOREIGN PATENT DOCUMENTS 2131954  6/1984  United Kingdom .................. 435/29

OTHER PUBLICATIONS

L. Stryer, Biochemistry, 2nd ed., W. H. Freeman & Co., pp. 110–116.

Primary Examiner—John Niebling
Assistant Examiner—Arun S. Phasge
Attorney, Agent, or Firm—Dunlap, Codding & Lee

[57] ABSTRACT

A device and method for detecting and/or continuously measuring the concentration of oxidizable biodegradable substrates in a medium. The device comprises an oxygenated first electrode and a second electrode. The first electrode is capable of carrying microorganisms capable of oxidizing the substrates in the presence of oxygen thus releasing electrons. The electrons are received by the second electrode and detected and/or measured by the device. The rate of electron transfer correlates to the concentration of substrate in the medium providing a method of continuous measurement of the substrate in the medium.

8 Claims, 4 Drawing Sheets

DEVICE FOR DETECTING AND CONTINUOUSLY MEASURING THE CONCENTRATION OF OXIDIZABLE BIODEGRADABLE SUBSTRATES IN A MEDIUM AND METHOD

FIELD OF THE INVENTION

The present invention generally relates to devices comprising electrodes and methods of use, and, more particularly, to devices and methods for detecting the presence of oxidizable biodegradable substrates such as organic compounds in a medium.

SUMMARY OF THE INVENTION

The present invention comprises a detecting device comprising a first electrode, a second electrode, means for oxygenating a portion of the first electrode and means for detecting electron transfer between the electrodes.

The first electrode comprises a first conducting element conductively connected to a first conductor. The first conducting element is capable of carrying an effective amount of a microorganism capable of oxidizing oxidizable biodegradable substrate in the presence of an effective amount of oxygen such that electrons are emitted therefrom. The microorganism carried by the first electrode is exposable to the substrate.

The second electrode comprises a second conducting element conductively connected to a second conductor. The second electrode is capable of receiving electrons from the first electrode.

The first conducting element is oxygenated by any means such that an effective amount of oxygen is providable for oxidizing the substrate at the first conducting element. Electron transfer between the electrodes is detected by any appropriate means.

The present invention further comprises using the above described device in a method for detecting the presence of oxidizable biodegradable substrate in a medium. The first and second electrodes of the measuring device are disposed in the medium for a sufficient amount of time for an effective number of microorganisms contained in the medium to migrate to the first conducting element. The electron flow between the electrodes is detected.

The present invention further comprises an electrode connectable to an external circuit which is capable of measuring electrical current. The electrode comprises a conductor conductively connected to a conducting element comprising an activated carbon plug.

BRIEF DESCRIPTION OF THE DRAWINGS

FIG. 6 shows a graph of a microamp reading plotted against the Biochemical Oxygen Demand (BOD) of a sewage sample using the device of the present invention.

DETAILED DESCRIPTION OF PREFERRED EMBODIMENTS

There is often a need to determine the presence of and/or the concentration of oxidizable biodegradable substrates in mediums. Examples of oxidizable biodegradable substrates in mediums are organic waste material in sewage, or organic waste material in streams, lakes, rivers, or other types of water reservoirs. "Medium" as used herein means a fluid, preferably a water-based fluid, such as a solution or suspension. The medium can be static or in motion.

Presently, the Biochemical Oxygen Demand test or the Chemical Oxygen Demand test is used to measure the amount of oxidizable biodegradable substrates (hereafter "the substrate") in a medium. These tests not only take days or hours, respectively, to determine the amount of substrate in the medium, but also are incapable of providing a continuous measurement. The present invention provides a spontaneous detector of oxidizable biodegradable substrates in a medium, and an inexpensive, continuous monitor of the concentration of oxidizable biodegradable substrates in a medium.

The present invention also provides a way in which toxic substances in the medium can be rapidly detected. This has practical application, for example, in the rapid detection of or continuous monitoring for toxic waste discharges in water reservoirs.

Figure 1:
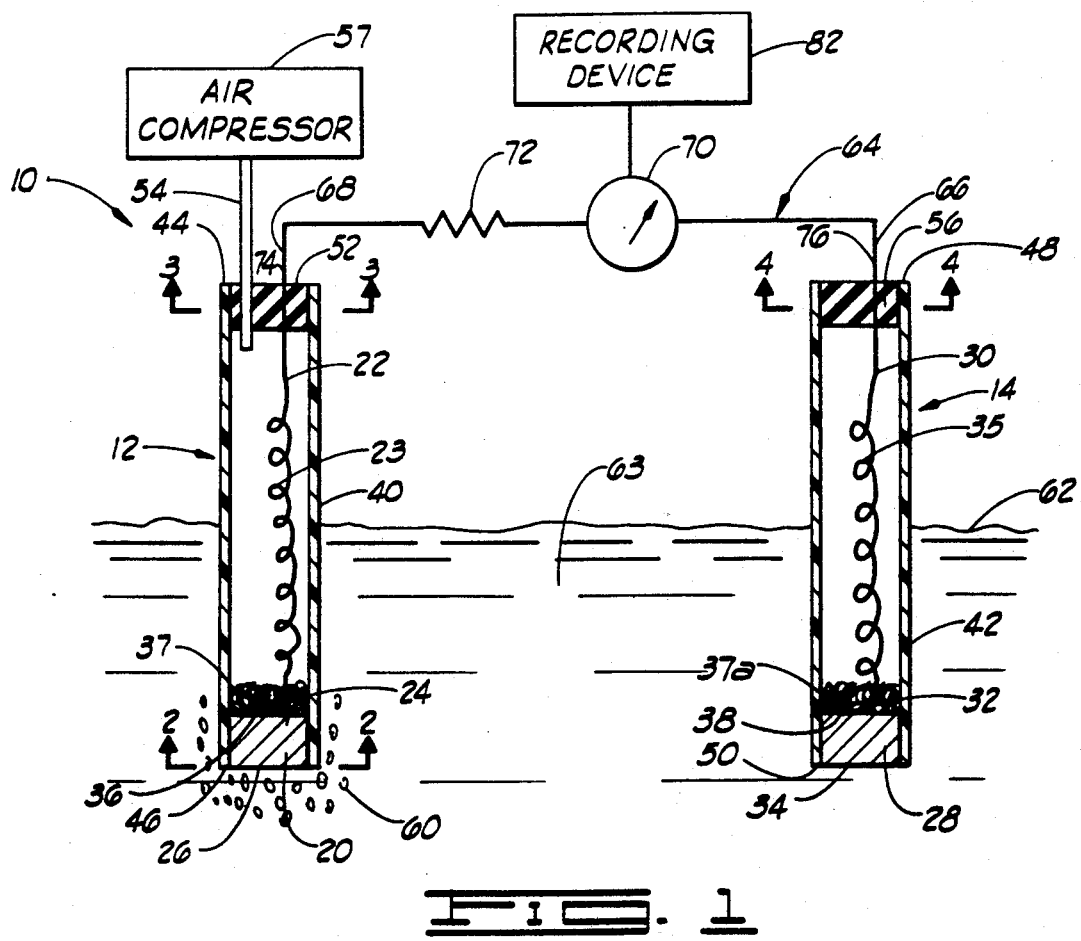
FIG. 1 shows an elevational view of the device of the present invention in a medium to be monitored.

Referring to FIG. 1, the device 10 of the present invention comprises a first electrode 12 and a second electrode 14 connected such that the electrical current therebetween can be measured. Preferably, the electrodes 12 and 14 of the present invention are constructed from substantially the same materials in order to eliminate any unwanted voltages. The first electrode 12 is the site of production of the electrons, and the second electrode 14 receives the electrons emitted by the first electrode 12. It is to be understood that the electron transfer described herein is from electrode 12 to electrode 14 through the medium.

The first electrode 12 of the present invention comprises a first conducting element 20 and a first conductor 22. In a preferred embodiment, the first conducting element 20 has an upper face 24 and a lower face 26, and is generally circular in cross-section. The first conductor 22 comprises a wire capable of conducting electrons. A portion of this wire may form a first spring 23 as shown in FIG. 1. An example of suitable material from which the first conductor 22, including the spring 23, may be formed is 310 Stainless Steel.

Likewise, the second electrode 14 comprises a second conducting element 28 and a second conductor 30. In a preferred embodiment, the second conducting element has an upper face 32 and a lower face 34 and is generally circular in cross-section. The second conductor 30 comprises a wire capable of conducting electrons. A portion of this wire may form a second spring 35 as shown in FIG. 1. The second conductor 30 and the second spring 35 are preferably constructed from the same materials as the first conductor 22 and first spring 23.

The first spring 23 and the second spring 35 are constructed such that a sufficient constant pressure is applied to the upper surface of respective conducting elements 24 and 32 to insure a contact sufficient to conduct electricity through the springs 23 and 35 to or from the conducting elements 24 and 32 in a consistent manner, i.e., the conducting elements 24 and 32 are conductively connected respectively to conductors 20 and 30.

The first conducting element 20 is sufficiently sized and has the ability to carry an effective amount of a selected microorganism capable of oxidizing a sufficient quantity of the substrate from the medium in the presence of oxygen. Further, the first conducting element 20 is sufficiently porous to permit gases such as oxygen to permeate therethrough in a sufficient quantity to provide an effective amount of oxygen for the substrate oxidation process. Preferably, the first conducting element 20 and the second conducting element 28 are constructed from the same material.

"Carrying" the microorganism as used herein means that the microorganism is located at (on and/or in) the first conducting element 20. An "effective amount" of the selected microorganism is an amount which generally saturates the first conducting element 20 to the extent that a steady state is reached and an electrical current detected by the device 10. A "steady state" is reached when the microorganism in the device 10 of the present invention continues to emit the same amount of electrical current for a known given concentration of substrate for a period of time, such as one week. It is believed that the microorganism is continually replenished in the first conducting element 20 by the supply of microorganisms present in the medium.

"Selected microorganism" is the microorganism which can oxidatively biodegrade the substrate from the medium in the presence of oxygen. An example of a selected microorganism is the microorganism or microorganisms normally found in the medium to be monitored, such as sewage. Typically, an oxygenated first conducting element 20 is exposed to the medium which is to be monitored. The selected microorganism (which may include several species of microorganisms) will migrate to and grow at (on and/or in) the first conducting element 20 until a steady state is reached and an electrical current is detected in the device 10. This can take from about 3 days to about 3 weeks. It is at this point, that an effective amount of the microorganism is carried by the first conducting element 22 of the present invention. If the selected microorganism is known, it can be introduced to the first conducting element 20 by any appropriate method.

In a preferred embodiment, the conducting elements 20 and 28 comprise activated carbon plugs. One source of activated carbon plugs is soft wood charcoal treated with a sufficient amount of microwave energy. The soft wood charcoal is preferably enclosed in a radiation transparent and heat resistant container such as a porcelain drying dish with a lid so that the soft wood charcoal is processed in an oxygen free atmosphere. After the treatment of the charcoal for a sufficient amount of time in the microwave, the electrical resistance drops from several kilo ohms per cm in the untreated soft wood charcoal to a conducting state of several ohms per cm in the preferred treated condition to provide an activated carbon plug.

During this process, the softwood charcoal gradually looses any residual volatiles. The carbon undergoes a partial change from amorphous form to a graphitic form. This treatment renders the carbon surfaces more adsorbent and improves the electrical conductivity of the carbon. This treatment forms a unitary activated electrically conductive carbon plug which is porous and retains an inherent wood grain pattern.

Preferably, the electrodes 12 and 14 are then shaped into a cylindrical shape from the treated charcoal having a generally circular cross-section. The activated carbon plug is shaped so that selected microorganism and substrate can access the carbon plug from the conducting element lower face 26, e.g. when the grain of the wood is about a 90 degree angle (substantially perpendicular) to the conducting element lower face 26. This permits the natural intercommunicating pore structure of the activated carbon plug to provide the air passages necessary for the gases to permeate therethrough, and allows greater area exposure for contacting the substrate. Although not limited to these dimensions, in a preferred embodiment, the carbon plug has a diameter of 1 cm and a length of 0.5 cm.

At least the lower faces 26 and 34 of the respective conducting elements 20 and 28 are preferably treated with a hydrophobic agent to substantially prevent the medium to be monitored from excessively infiltrating and thereby damaging the electrodes 12 and 14. However, this hydrophobic agent permits the passage of the microorganism and the substrate from the medium.

One example of a hydrophobic agent used in accordance with the present invention is 0.1 gm of paraffin combined with 1 ounce of a lighter fluid or other petroleum distillate. The hydrophobic agent is applied to the conducting elements 20 and 28, preferably by dipping the conducting elements 20 and 28 into the hydrophobic agent or by brushing the hydrophobic agent onto the conducting elements 20 and 28, and then blowing air therethrough. Any other blocking agent may be used to protect the conducting elements 20 and 28 in accordance with the present invention which permits the operation of the device 10 as described herein.

The conductors 22 and 30 are respectively connected to the conducting elements 20 and 28 such that electrons may be conducted therethrough. As shown in FIG. 1, the first conducting element upper face 24 contacts a lower terminal end 36 of the first conductor 22. Between the lower terminal end 36 and the conducting element upper face 24, stainless steel wool 37 is disposed in an amount sufficient to enhance electrical conductive contact between the first conducting element upper face 24 and the first conductor 22. Likewise, the second conducting element upper face 32, contacts the lower terminal end 38 of the second conductor 30. Between the lower terminal end 38 and the second conducting element upper face 32 stainless steel wool 37a is disposed in an amount sufficient to enhance electrical conductive contact between the second conducting element upper face 32 and the second conductor 30.

Although the conducting elements 20 and 28 may be placed directly into the medium to be monitored, in a preferred embodiment, the conducting elements 20 and 28 are encased in housings such as open ended tubes 40 and 42, preferably constructed from plastic. Referring to FIG. 1, first tube 40 comprises an upper end 44 and a lower end 46 with a consistent circular cross section throughout. Second tube 42 comprises an upper end 48 and a lower end 50 with a consistent circular cross section therethrough. The housing tubes 40 and 42 provide stability to the device 10 and prevent excessive exposure of the medium to the conducting elements 20 and 28 and conductors 22 and 30 partially enclosed therein. Additionally, preferably pressure inside the housings 40 and 42 provided by gases such as oxygen and/or fluids such as clean water, can prevent the medium from substantially entering the housings 40 and 42.

Figure 2:
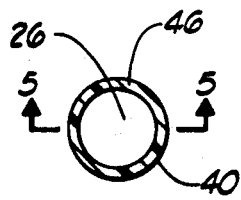
FIG. 2 shows a bottom view of one of the electrodes shown in FIG. 1.

The inner diameter of each tube 40 and 42 is respectively sized to frictionally receive the conducting elements 20 and 28, and is longitudinally sized to respectively enclose the conducting elements 20 and 28 and the conductors 22 and 30. FIG. 2 shows a bottom view of the first conducting element 20 in the first tube 40, which is also typical of the position of the second conducting element 28 in the second tube 42. The conducting elements 20 and 28 can be respectively secured in tubes 40 and 42 by any additional means such as gluing if necessary.

Figure 3:
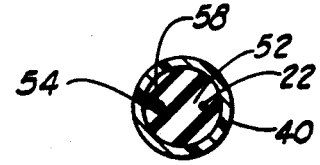
FIG. 3 shows a cross section of the top portion of one of the electrodes of FIG. 1 taken at 3—3.

Referring to FIGS. 1 and 3, the first tube upper end 44 has disposed therein a first plug 52 with appropriately sized apertures to permit frictional passage of the first conductor 22 and the air duct 54. The first plug 52 is sized to frictionally fit in the first tube upper end 44 and to seal same.

Figure 4:
FIG. 4 shows a cross section of the top portion of the electrodes of FIG. 1 taken at 4—4.
Figure 5:
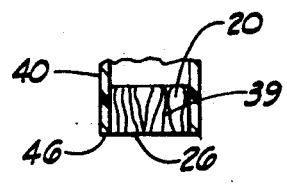
FIG. 5 shows a cross section of the first conducting element in FIG. 2 taken at 5—5.
Figure 5:
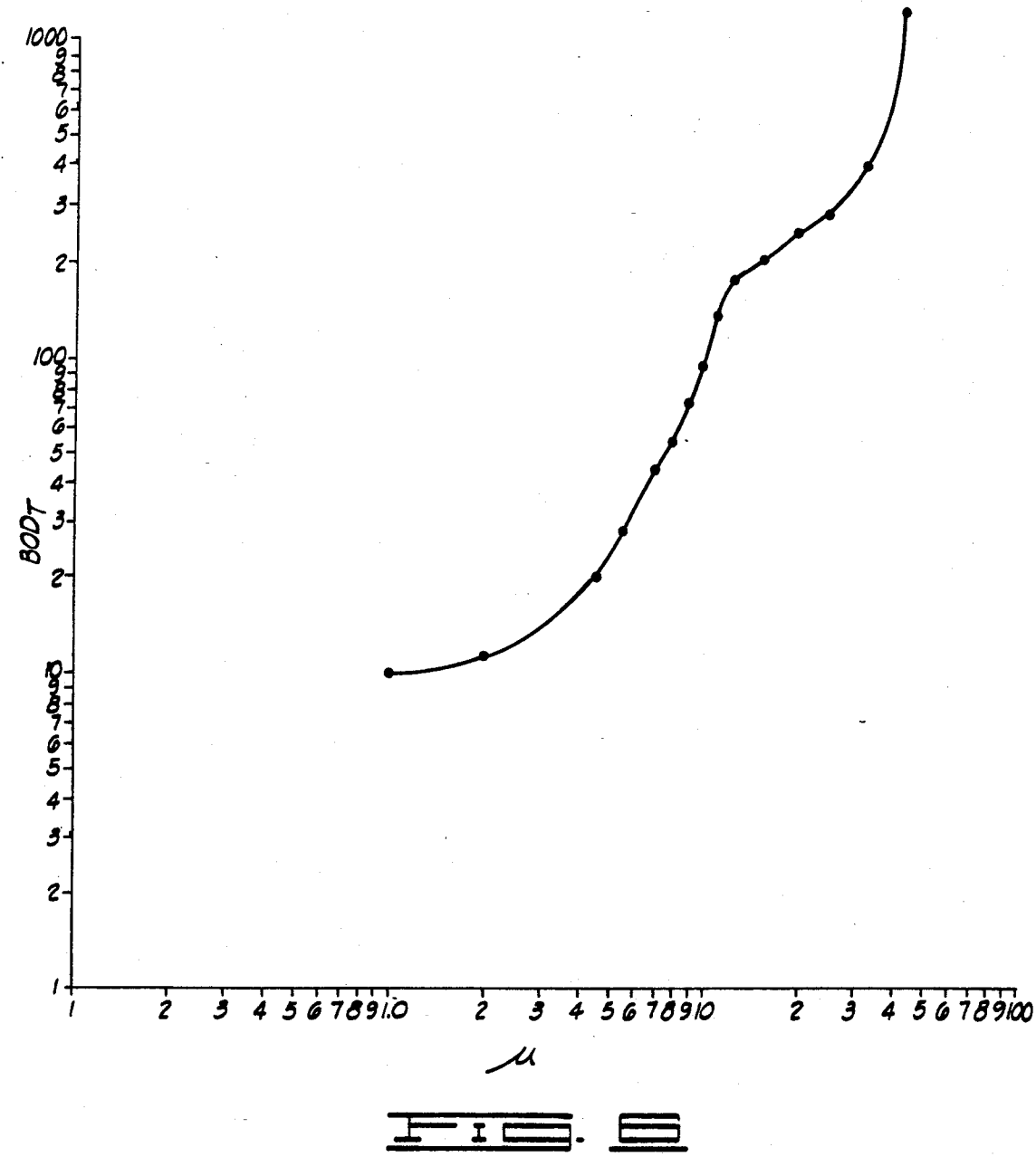

Likewise, referring to FIGS. 1 and 4, the second tube upper end 44 has disposed therein a second plug 56 with an appropriately sized aperture to permit passage of the second conducting wire 38. The second plug 56 is sized to frictionally fit in the second tube upper end 52 and to seal same.

The plugs 52 and 56 function to seal, and thus protect, the electrodes 12 and 14. Sealing the first electrode 12 also prevents escape of oxygen supplied thereto through the upper end 44 of the first tube 40.

The first electrode 12 is sufficiently oxygenated in order to provide a sufficient amount of oxygen for oxidative biodegradation of the substrate. In a preferred embodiment shown in FIG. 1, an air duct 54 having an aperture 58 for the passage of gas is passed through the first plug 52 disposed in the first tube upper end 44. Since the second conducting element 28 is not oxygenated, little or no microbial growth occurs at the second conducting element 28.

Oxygen, usually in the form of compressed air, is forced through the air duct 54 by any means such as an air compressor 57 as schematically shown in FIG. 1, at a rate which forces a sufficient amount of oxygen through the first conducting element 20. Air bubbles 60 in the medium 62 can be observed when the first conducting element 20 has been sufficiently oxygenated for the purposes of the present invention. An air duct 54 used in accordance with the present invention is a tube having an inside diameter of approximately 1.5 cm.

In a preferred embodiment, oxygen is supplied via an air compressor 57 such as that used to supply air to an aquarium or for aerating laboratory samples. The air pressure, sufficient to overcome the water pressure at the surface of the first conducting element lower face 26, is about 2 psi. The first conducting element lower face 26 in this example is submerged 3-5 inches below the surface 62 of the medium 63. The volume of air released provides a dissolved oxygen concentration at electrode 20. A small stream of bubbles 60 escaping from electrode 20 accomplishes this. Since large excesses of bubbles 60 on the first conducting element lower face 26 can also reduce the electric current flow through the device 10, electrodes 12 and 14 are disposed in the medium 63 at an angle of 20°-30° from the vertical so that any air bubbles 60 formed at the first conducting element lower face 26 will be able to escape quickly.

The electrodes 12 and 14 are connected together through an external circuit 64 such that an electrical current between the electrodes 12 and 14 can be measured. Preferably, the external circuit 64 comprises a first conducting wire 66, a second conducting wire 68, an ammeter 70 and a variable resistor 72. The first conducting wire 66 is connected at one end 74 to the portion of the first conductor 22 coming out of first electrode 12 through first plug 52. The second conducting wire 68 is connected at one end 76 to the portion of the second conductor 30 coming out of the second electrode 14 through second plug 56. The first conductor 22 and the first conducting wire 68 may be one continuous wire. The second conductor 30 and the second conducting wire 68 may be one continuous wire.

The second conducting wire other end 78 is connected to the ammeter 70 and then the resistor 72 and then the other end 80 of the first conducting wire 66. In this fashion, electrons emitted from the first conducting element 20 are collected by the second conducting element 28 and transmitted through the second conductor 30, through the second conducting wire 69 to the ammeter 70 where the rate of electron transfer is measured.

In operation in a preferred embodiment, the electrodes 12 and 14 are disposed in a stream of raw sewage for approximately 3 weeks as shown in FIG. 1, except the electrodes 12 and 14 are disposed at a 20°-30° angle to the vertical position shown in FIG. 1. During this time, the first electrode 12 is continuously oxygenated at a pressure of about 2 psi. The microammeter 70 is observed until an electrical current is detected. If a permanent graphic record is desired then a strip chart recorder 82 can be used.

In this fashion the device 10 of the present invention can detect the presence of the substrate in the medium, and can monitor relative changes in the substrate concentration of the medium. In order to measure the substrate concentration, the device 10 is calibrated, as described hereafter. Once the device 10 is calibrated, the electrodes 12 and 14 remain in the medium to be monitored while oxygen is continuously pumped into the first electrode 12. Calibration occurs after a steady state of microorganisms has been reached in the first conducting electrode 22.

Since the device 10 of the present invention uses live microorganisms to initiate the electron transfer from the substrate, toxic materials released in the medium capable of killing at least a portion of the microorganisms can be detected by the device 10. Thus the device 10 of the present invention can be used as a monitoring device to determine whether toxic materials are released into a medium and even determine when the materials are released if the device 10 is connected to a strip feed having specified time intervals shown thereon.

The device and method of the present invention are further illustrated by preferred embodiments of the following examples. The present invention is not limited, however, to the examples shown herein.

EXAMPLE 1

Preparation of activated carbon conducting elements.

A block ½"×1"×4" of wood charcoal with the grain running parallel to the length is obtained from a chemical supply store. The block is cut into ½" section and the cut sections placed in a porcelain drying dish with a porcelain cover.

The drying dish with top is then placed in a 750 watt microwave oven, set so that the power is on approximately ½ of the time and off ½ of the time for a total time of approximately 70 minutes. After treatment the charcoal blocks are allowed to cool.

After cooling, the blocks are tested with a multimeter set to register resistance in ohms. Prior to treatment, the charcoal block have a very high resistance, commonly several thousand ohms/cm or more. After successful microwave treatment the electrical resistance is reduced to 10 to 20 ohms/cm.

EXAMPLE 2

Calibration of device of the present invention

Preliminary calibration of the device 10 of the present invention was accomplished by compiling the microamp output of the electrodes immersed in a sewage sample, and then plotting this $\mu A$ reading against the biochemical oxygen demand of the same sample, determined by the approved 5 day BOD method.

After several weeks of accumulating data, sufficient points were established to provide a curve. Table 1 and the graphs shown in FIGS. 6 and 7 of $\mu A$ (micro amps) vs. BOD is the result.

TABLE 1

| $1/\mu$ | $\mu$ | $1/BOD_T$ | $BOD_T$ |
|---|---|---|---|
| 23 | 43.5 | 0 | ∞ |
| 25 | 40.0 | 0.8 | 1250 |
| 30 | 33.3 | 2.5 | 400 |
| 35 | 28.6 | 3.2 | 312 |
| 40 | 25 | 3.5 | 286 |
| 45 | 22 | 3.75 | 267 |
| 50 | 20 | 4.0 | 250 |
| 55 | 18 | 4.3 | 232 |
| 60 | 17 | 4.6 | 217 |
| 65 | 15.4 | 4.85 | 206 |
| 70 | 14.3 | 5.15 | 194 |
| 75 | 13.3 | 5.4 | 185 |
| 80 | 12.5 | 5.7 | 175 |
| 85 | 11.8 | 6.0 | 167 |
| 90 | 11 | 7.5 | 133 |
| 100 | 10 | 10.5 | 95 |
| 105 | 9.5 | 12.1 | 82.6 |
| 110 | 9.0 | 13.7 | 73 |
| 115 | 8.7 | 15.2 | 66 |
| 120 | 8.3 | 16.7 | 60 |
| 125 | 8.0 | 18.2 | 55 |
| 130 | 7.7 | 19.7 | 51 |
| 140 | 7 | 22.7 | 44 |
| 150 | 6.6 | 26.7 | 37.5 |
| 180 | 5.5 | 34.9 | 28.6 |

Figure 7:
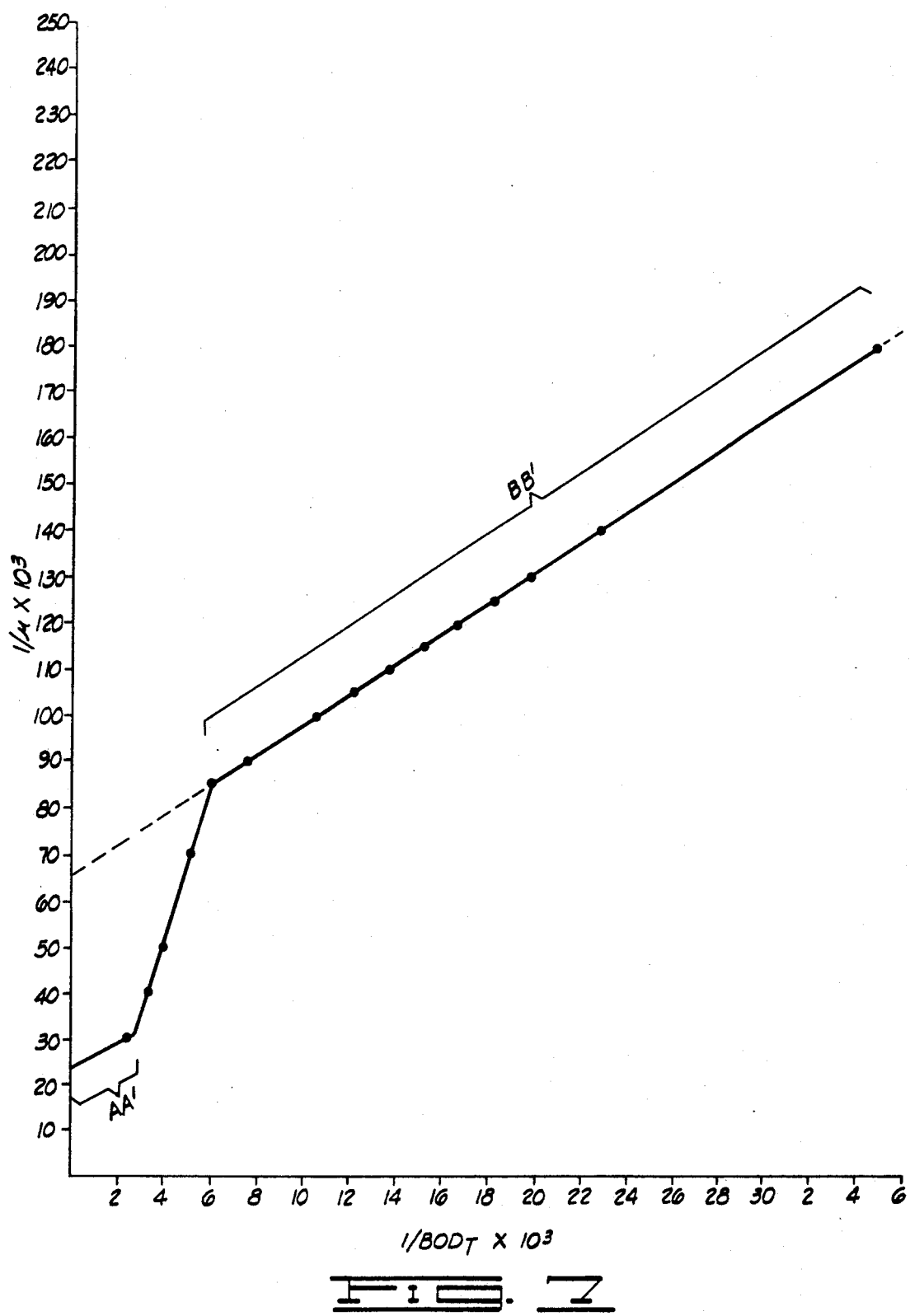
FIG. 7 shows a graph plotting reciprocals of data in FIG. 6.

Mathematical analysis of this curve, with the assumption that the rate of oxidation is related to the substrate concentration in a manner similar to that postulated by Michealis and Menton (see L. Stryer, *Biochemistry*, 2nd ed., W. H. Freeman & Co., New York, pp. 110–116, incorporated herein by reference), has led to the plotting of the reciprocals of the original raw data. This reciprocal data is shown in Table 1 and the graph shown in FIG. 7. Referring to FIG. 7, this date was taken from raw data except for the AA' line which tops out at $1/42 \times 10^{-6}$ amps and is assumed to be parallel with BB' for Dextrose.

Analysis of the data shows that oxidation takes place at least at two rates: one rate when the microamp current is less than about 12 $\mu A$, and another at $\mu A$ currents above 12 $\mu A$. This means of calibration works well for any single set of probes and the accompanying external circuit. However, since the total internal resistance of each complete measuring system, i.e., electrodes plus meter, is different, a variable resistance is included in the external circuit.

Using this circuit, calibration can be accomplished by immersing the electrodes in sugar mediums of 3 or more known concentrations and adjusting the internal resistance of the system to closely match the original calibration curve. This can be easily accomplished graphically with only a few points if the reciprocal data is plotted, since the reciprocal data plot results in a straight line.

Figure 8:
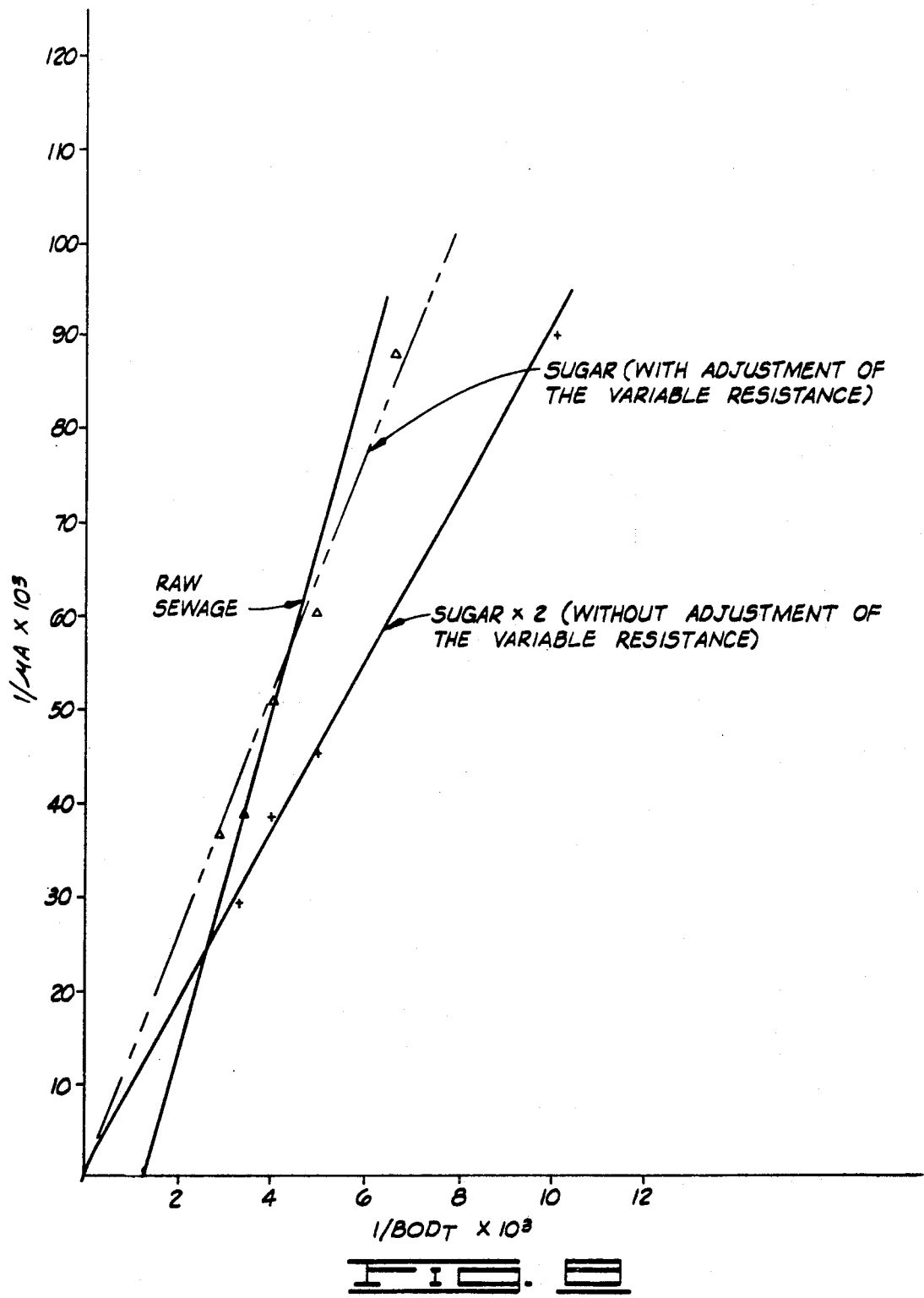
FIG. 8 shows a graph plotting known sugar concentrations and raw sewage for purposes of calibrating the device of the present invention.

Table 2 and the graph shown in FIG. 8 ($1/\mu A \times 10^3$ vs. $1/BOD_T \times 10^3$) show the result of this form of calibration using sugar (i.e., common table sugar) producing results that are not quite the same as sewage but the results are near enough to be useful.

TABLE 2

| SUGAR SOLUTION INITIAL DATA | | | | | | |
|---|---|---|---|---|---|---|
| TOTAL BOD | 100 | 150 | 200 | 250 | 300 | 350 |
| $\mu A$ | 11 | 15 | 22 | 26 | 34 | 36 |
| $1/\mu A \times 10^3$ | 90.9 | 66.7 | 45.5 | 38.5 | 29.4 | 27.8 |
| WITH ADJUSTMENT OF VARIABLE RESISTANCE (72) | | | | | | |
| $1/\mu A$ | 121.2 | 88.8 | 60.6 | 51.3 | 39.2 | 37 |

| RAW SEWAGE DATA FOR COMPARISON WITH CALIBRATION USING SUGAR AS SHOWN IN FIG. 8 | | | |
|---|---|---|---|
| $BOD_T$ | $1/BOD_T$ | $\mu A$ | $1/\mu A$ |
| 95 | 10.5 | 10 | 100 |
| 133 | 7.5 | 11 | 90 |
| 167 | 6.0 | 11.8 | 85 |
| 185 | 5.4 | 13.3 | 75 |
| 206 | 4.85 | 15.4 | 65 |
| 232 | 4.3 | 18.0 | 55 |
| 267 | 3.75 | 22 | 45 |
| 312 | 3.2 | 28.6 | 35 |
| 400 | 2.5 | 33.3 | 30 |

Changes may be made in the construction, operation and arrangement of the various parts, elements, steps and procedures described herein without departing from the spirit and scope of the invention as defined in the following claims.

What is claimed is:

1. A detection device for detecting oxidizable biodegradable substrates in a medium having microorganisms therein comprising:
   a first electrode comprising:
      a first tube having an upper end and a lower end and an opening extending therethrough intersecting the upper and the lower ends thereof;
      a first conducting element having an upper face and a lower face, and being disposed in the opening in the first tube and positioned at the lower end of the first tube, the first conducting element being porous, the first conducting element being positioned in the tube so that the lower face of the first conducting element is exposed to the medium when the first electrode is at least partially immersed in the medium;
      a first conductor connected to the first connecting element, the first conductor extending through the opening in the tube;
   a second electrode;
   air compressor means for passing air having oxygen therein into the opening in the first tube, a portion of the compressed air passing through the first conducting element and the compressed air in the first tube substantially preventing the medium from passing through the first conducting element and into the opening in the first tube, the microorganisms in the medium associated with the first conducting element oxidizing the biodegradable substrate in the presence of oxygen passed from the air compressor means associated with the first conducting element and causing electrons to be emitted from the first conducting element, the electrons passing through the medium and the second electrode; and means connected to the first conductor and the second electrode for detecting electron transfer between the first and second electrodes thereby indicating the oxidizable biodegradable substrates in the medium.

2. The device of claim 1 in which the first conducting element comprises an activated carbon plug.

3. The device of claim 2 in which the activated carbon plug comprises a wood grain pattern, in which the direction of the pattern is at about a 90 degree angle to the lower face portion of the carbon plug.

4. The device of claim 1 further comprising blocking means for treating the first and second conducting elements to prevent a substantial amount of the medium from passing into the openings in the first and second tubes when the electrodes are at least partially immersed in the medium.

5. The device of claim 1 wherein the first electrode further comprises:

a first plug disposed in the opening in the first tube at the upper end of the first tube for sealingly closing the upper end of the first tube.

6. The device of claim 1 wherein the second electrode further comprises:

a second tube having an upper end and a lower end and an opening extending therethrough and intersecting the upper and the lower ends thereof;

a second conducting element having an upper face and a lower face and being disposed in the opening in the second tube and positioned at the lower end of the second tube, the second conducting element being porous, the second conducting element being positioned in the second tube so that the lower face of the second conducting element is exposed to the medium when the second electrode is at least partially immersed in the medium; and a second conductor connected to the second conducting element, the second conductor extending through the opening in the second tube.

7. The device of claim 6 in which the second conducting element comprises an activated carbon plug.

8. The device of claim 6 wherein the second electrode further comprises:

a second plug disposed in the opening in the second tube at the upper end of the second tube for sealingly closing the upper end of the second tube.

* * * * *

UNITED STATES PATENT AND TRADEMARK OFFICE
CERTIFICATE OF CORRECTION

PATENT NO. : 5,158,662
DATED : October 27, 1992
INVENTOR(S) : Osborne

It is certified that error appears in the above-indentified patent and that said Letters Patent is hereby corrected as shown below:

Column 7, line 54, please delete the word
    "date" and substitute therefore the word
    --data--.

Column 8, line 56, please delete the word
    "connecting" and substitute therefore the
    word --conducting--.

Signed and Sealed this

Fifth Day of October, 1993

*Attest:*

BRUCE LEHMAN

*Attesting Officer*     *Commissioner of Patents and Trademarks*